United States Patent [19]
Cain et al.

[11] Patent Number: 6,127,562
[45] Date of Patent: Oct. 3, 2000

[54] PROCESS FOR THE ENRICHMENT OF COMPOUNDS IN TRANS-10 ISOMERS

[75] Inventors: Frederick William Cain; Michel Henrias Wilhelmus Van der Hoek; Victoria Taran, all of Wormerveer, Netherlands

[73] Assignee: Loders Croklaan B.V., Wormerveer, Netherlands

[21] Appl. No.: 09/310,339

[22] Filed: May 12, 1999

[30] Foreign Application Priority Data

May 12, 1998 [EP] European Pat. Off. ............... 98201580

[51] Int. Cl.[7] ....................................................... C11B 7/00
[52] U.S. Cl. ................................................................. 554/175
[58] Field of Search ............................................. 884/175

[56] References Cited

FOREIGN PATENT DOCUMENTS

WO 96/37586  11/1996  WIPO ............................. C11B 7/00
WO 96/37587  11/1996  WIPO ............................... C11C 1/04
WO 97/18320  5/1997   WIPO ............................... C12P 7/64

OTHER PUBLICATIONS

Chemical Abstracts, vol. 112, No. 12 (1990), Abstract No. 174637.

Chemical Abstracts, vol. 111, No. 9 (1989), Abstract No. 73700.

*Primary Examiner*—Deborah D. Carr
*Attorney, Agent, or Firm*—Pillsbury Madison & Sutro LLP

[57] ABSTRACT

PUFA mixtures containing different isomers with at least two conjugated unsaturations, including trans-10 double bonds can be enriched in the trans-10 isomers by subjecting the mixture to an enzymic conversion in the presence of an enzyme with trans-10 specificity followed by separation of the reaction mixture and isolation of the enriched product.

18 Claims, No Drawings

PROCESS FOR THE ENRICHMENT OF COMPOUNDS IN TRANS-10 ISOMERS

In our earlier patent application WO 97/18320 we have disclosed a method, based on alcoholysis (so including glycerolysis) for the enrichment of a compound (such as CLA) comprising different geometrical isomers of polyunsaturated fatty acids in one of these isomers by subjecting a starting composition to an enzymatic treatment with an enzyme having specificity for one of these isomers. This alcoholysis route enables us to make compositions that are enriched in specific desired isomers, including trans-10 isomers. However above process is not very suitable to obtain an ester product that is enriched in trans-10 isomers. This is caused by the fact that the enzymes disclosed in this earlier patent application can only be used for an enrichment in trans-10 isomers along the free fatty acid route. If an enrichment in the trans-10 isomer is required in the esters first a free fatty acid product has to be made that is then converted into the esters and this process has to be repeated several times. This makes that this process is complicated and leads to lower enrichment. Therefore we have studied whether we could find other routes with which an ester product, enriched in trans-10 isomers could be made in one esterification step resulting in higher enrichment.

Above study resulted in our invention, wherein known enzymes are applied from which it was not known that they have trans-10 specificity. Therefore our invention concerns in the first instance a process for the enrichment of a polyunsaturated fatty acid (=PUFA) mixture, comprising different isomers with at least two conjugated unsaturations, including isomers from which one unsaturation is a trans-10 double bond,

- the PUFA-mix in particular being a CLA-mixture, comprising different CLA-isomers, but at least including CLA-isomers with a trans-10 double bond,
- in polyunsaturated isomers having a trans-10 double bond, in particular in CLA-isomers with a trans-10 double bond,
- wherein the PUFA-mix comprising at least 5 wt % of trans-10 isomer, in particular at least 5% of the trans-10 CLA-isomer is subjected to an enzymatic conversion with a mono-, di- or higher alcohol using an enzyme that can discriminate trans-10 isomers from other cis and/or trans isomers also present in the PUFA-mix, in particular the CLA mixture
- and separating the mixture obtained after the conversion into unconverted PUFA-acids, in particular CLA and esters or glycerides from the PUFA-acids, in particular the CLA by physical or chemical means
- and isolating an ester or glyceride mix from PUFA's, in particular from CLA's that is enriched in the trans-10 PUFA-isomers, in particular the CLA-isomers with at least 10%, preferably at least 20% more preferably at least 30% compared to the starting mixture.

Our new process is particularly useful, when using short alkyl alcohols (C1–C6), preferably ethanol and glycerol, that are foodgrade.

Enzymes that are preferred for our purposes are 1) lipases derived from Alcaligenes and having a molecular weight measured by gel filtration of less than 250,000 or
2) a lipase derived from *Pseudomonas cepacia*.

These enzymes are commercially available e.g. from Meito Sangyo CO. However it was not known that these enzymes can discriminate trans-10 isomers from other cis and trans isomers.

The process is performed at 20–80° C., preferably at 30–55° C. most preferably at 40–50° C. The water formed during this process can be removed from the reaction mix. Methods to do this are well known and include a vacuo treatment, or the use of a water binder such as a molecular sieve or the use of an inert stripping gas. In this way the water content of the reaction mix can be maintained at 1–4 wt % during the conversion.

The separation of unconverted PUFA-isomers, in particular the CLA-isomers and PUFA-esters, in particular the CLA-esters formed is performed by molecular destination and/or by forming salts of the free PUFA-isomers, in particular CLA-isomers and removal of the salts formed.

The starting materials applied for the conversion are preferably based on a PUFA-mix, in particular a CLA-mix containing more than 20 wt %, preferably more than 30 wt % of the trans-10 PUFA-isomers, in particular the trans-10 CLA-isomers, based on the total PUFA-mix, in particular the total CLA-mix.

Particularly preferred starting materials comprise trans-10cis-12 isomers and cis-9trans-11 isomers in about equimolecular amounts.

The processing can be performed until a limited conversion is achieved or until at least one of the components of the reaction mix is completely converted. This will depend on the fact whether the mole ratio PUFA-isomers (or CLA isomers):alcohol applied is equivalent or not. In case the mole ratio PUFA-isomers:alcohol is above equimolecular the conversion will be about completed. If however this ratio is below equimolecular this conversion will be limited to below 80%, preferably below 70%, of PUFA-isomers applied.

EXAMPLES

1. Preparation of Starting Composition CLA 1:1 Mix of c9t11 and t10c12

150 G of NaOH was dissolved in 1600 g of propyleneglycol by heating at 60° C. Than the temperature was increased to 90° C. and 523 g of safflower oil was added to this mix. After that the temperature was raised until 135° C. The mixture obtained was stirred at 135° C. under N2 for 40 hrs. The mixture was cooled to 90° C. and the soap formed was split with 1.2 l sulphuric acid (10 Vol %). The pH of the mixture was 3.0. The oil obtained was washed three times with hot water, each time with 1 l of water. pH of the water after last washing was 7.0. The oil was dried under vacuum at 80° C. 420 G of CLA was obtained. There was no water detected by Karl Fisher method in the end product. The composition of this CLA (measured by high resolution FAME) was:

| CARBON CHAIN | % |
| --- | --- |
| C16:0 | 6.77 |
| C18:0 | 2.70 |
| C18:1 | 14.34 |
| C18:2 | 6.01 |
| c9t11 | 33.81 |
| CLA1012CT | 0.39 |
| t10c12 | 33.66 |
| others CLA isomers | 2.08 |
| C22:0 | 0.24 |

II. Enrichment in t10c12 Isomer Using Different Enzymes

100 G of the CLA obtained in example I was mixed with 0.5 g of water. Samples of 10 g of above CLA/water mix were mixed with different lipases (0.5 wt % of enzyme on CLA) and the reaction was started by adding 2.02 ml of ethanol (96%) to each sample. The reaction mixture was stirred at 38° C. and after 2;4 and 24 hrs samples were taken and analysed. Herefore 1 ml of each sample was mixed with 1 ml of water and 2 ml of iso-octane. The mixture was strongly stirred for 1 min and the extracted oil in iso-octane was collected. After removal of the iso-octane the samples were analysed on free fatty acid content by titration with 0.2 N NaOH and on isomer content after conversion of the ethyl esters into methyl esters by FAME analysis.

The results are summarised in the table below:

TABLE

| Lipase applied | conversion % | conv. time hours | ffa % | c9t11 % | t10c12 | c9t11/ t10c12 |
|---|---|---|---|---|---|---|
| ALCALIGENES spp* | 14.6 | 2 | 84.9 | 20.3 | 50.5 | 29:71 |
|  | 30.8 | 4 | 68.8 | 23.0 | 48.0 | 32:68 |
|  | 49.4 | 24 | 50.3 | 26.5 | 42.9 | 38:62 |
| SPEUDOMONES* | 24.4 | 2 | 81.5 | 26.4 | 41.7 | 39:61 |
|  | 35.2 | 4 | 69.8 | 27.2 | 41.1 | 40:60 |
|  | 58.8 | 24 | 44.4 | 29.8 | 38.2 | 44:56 |

*enzymes from Meito Sankyo Codes resp QL and SL

What is claimed is:

1. Process for the enrichment of a polyunsaturated fatty acid (=PUFA) mixture, comprising different isomers with at least two conjugated unsaturations, including isomers from which one unsaturation is a trans-10 double bond, in polyunsaturated isomers having a trans-10 double bond, wherein a PUFA-mix comprising at least 5 wt % of trans-10 isomer, is subjected to an enzymatic conversion with a mono- di- or higher alcohol using an enzyme that can discriminate trans-10 isomers from other cis and/or trans isomers also present in the PUFA-mix, and separating the mixture obtained after the conversion into unconverted PUFA-acids and esters or glycerides from the PUFA-acids by physical or chemical means and isolating an ester or glyceride mix from PUFA's that is enriched in the trans-10 PUFA-isomers with at least 10% compared to the starting mixture.

2. Process wherein the enzyme that can discriminate trans-10 isomers from other cis and/or trans isomers is a lipase derived from Alcaligenes and having a molecular weight measured by gel filtration of less than 250,000 or is a lipase derived from *Pseudomonas cepacia.*

3. Process according to claim 1, wherein the conversion is performed at 20–80° C.

4. Process according to claim 1, wherein water formed during the conversion is removed by vacuo or by adding a water binder.

5. Process according to claim 1 wherein the water content of the reaction mixture is maintained at 1–4 wt % during the conversion.

6. Process according to claim 1, wherein the separation of unconverted PUFA-isomers and PUFA-esters formed is performed by molecular distillation and/or by forming salts of the free PUFA-isomers and removal of the salts formed.

7. Process according to claim 1, wherein the PUFA-mix used as starting material contains more than 20 wt % of the trans-10 PUFA-isomers based on the total PUFA-mix.

8. Process according to claim 1, wherein the PUFA mix used as starting material is a CLA mixture comprising trans-10cis12 and cis-9 trans-11 isomers in about equimolecular amounts.

9. Process according to claim 1, wherein a mole ratio PUFA-isomers:(mono-, di- or polyalcohol) above the equimolecular ratio is applied while the PUFA-conversion is about completed.

10. Process according to claim 1, wherein a mole ratio PUFA-isomers:(mono-, di- or polyalcohol) below the equimolecular ratio is applied, while the conversion of the PUFA-isomers is kept below 80%.

11. Process according to claim 1, wherein the PUFA mix is a CLA mix comprising different CLA isomers but at least including CLA isomers with a trans-10 double bond.

12. Process according to claim 11, wherein the PUFA-mix used as starting material comprises at least 5 wt % of the trans-10 CLA isomer.

13. Process according to claim 12, wherein the isolated ester or glyceride mix is enriched in the trans-10-PUFA-isomers with at least 30% compared to the starting mixture.

14. Process according to claim 3, wherein the conversion is performed at 40–50° C.

15. Process according to claim 4, wherein the water is removed by using a molecular sieve.

16. Process according to claim 7, wherein the PUFA-mix used as starting material contains more than 30 wt % of trans-10 CLA-isomers.

17. Process according to claim 9, wherein the PUFA isomers are CLA-isomers.

18. Process according to claim 10, wherein the PUFA-isomers are CLA-isomers and wherein the conversion of the CLA-isomers is kept below 70%.

* * * * *